US008809007B2

(12) United States Patent
Christ et al.

(10) Patent No.: US 8,809,007 B2
(45) Date of Patent: Aug. 19, 2014

(54) METHOD FOR DETERMINING THE ACTIVITY OF A PROTEOLYTIC COAGULATION FACTOR IN A SAMPLE

(71) Applicant: Siemens Healthcare Diagnostics Products GmbH, Marburg (DE)

(72) Inventors: Gerlinde Christ, Marburg (DE); Andreas Kappel, Koenigstein (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 0 days.

(21) Appl. No.: 13/959,612

(22) Filed: Aug. 5, 2013

(65) Prior Publication Data

US 2013/0323765 A1   Dec. 5, 2013

Related U.S. Application Data

(63) Continuation of application No. 12/960,023, filed on Dec. 3, 2010, now Pat. No. 8,501,429.

(30) Foreign Application Priority Data

Dec. 9, 2009   (EP) ..................................... 09015240

(51) Int. Cl.
*C12Q 1/56*   (2006.01)

(52) U.S. Cl.
USPC .......................................................... 435/13

(58) Field of Classification Search
USPC ................................ 435/13; 424/141.1, 178.1
See application file for complete search history.

(56) References Cited

U.S. PATENT DOCUMENTS

| | | | |
|---|---|---|---|
| 4,409,327 A | 10/1983 | Bartl et al. ........................ | 435/13 |
| 4,480,030 A | 10/1984 | Svendsen ......................... | 435/13 |
| 4,508,644 A | 4/1985 | Heber et al. .................... | 530/331 |
| 4,598,043 A | 7/1986 | Svendsen ......................... | 435/13 |
| 4,668,621 A | 5/1987 | Doellgast ......................... | 435/13 |
| 4,859,581 A | 8/1989 | Nicolson et al. .................. | 435/4 |
| 5,102,787 A | 4/1992 | Sasamata et al. ............. | 435/7.21 |
| 5,348,942 A | 9/1994 | Little, II ........................ | 514/2.2 |
| 5,478,810 A | 12/1995 | Stuber et al. .................. | 514/13.6 |
| 5,866,350 A | 2/1999 | Canavaggio et al. ........... | 435/13 |
| 7,153,473 B2 | 12/2006 | Ericson et al. .................. | 422/44 |
| 8,501,429 B2 * | 8/2013 | Christ et al. .................... | 435/13 |
| 2003/0124622 A1 | 7/2003 | Roemisch et al. ............. | 435/7.4 |
| 2005/0236536 A1 | 10/2005 | Fan ........................... | 248/176.3 |

FOREIGN PATENT DOCUMENTS

| | | | | |
|---|---|---|---|---|
| EP | 0034320 A1 | 2/1981 | ............. | G01N 33/86 |
| EP | 0034122 A1 | 8/1981 | ............. | C07K 14/00 |
| EP | 0078764 A1 | 10/1982 | ............... | C12Q 1/56 |
| EP | 0456152 A2 | 5/1994 | ............... | C07K 7/06 |
| EP | 1396539 A1 | 3/2004 | ............. | C12N 15/09 |
| EP | 1624072 A1 | 2/2006 | ............... | C12N 1/37 |
| WO | 86/05591 A1 | 9/1986 | .......... | G01N 33/543 |
| WO | 99/00515 A1 | 1/1999 | ............... | C12Q 1/56 |
| WO | 01/44493 A2 | 6/2001 | ............... | C12Q 1/00 |

OTHER PUBLICATIONS

Mandi, Fakhri et al., "Protease Nexin-2/Amyloid βProtein Precursor Inhibits Factor Xa in the Prothrombinase Complex," The Journal of Biological Chemistry, vol. 270, No. 40, 7 pages, Aug. 3, 1995.
Al-Obeidi, F. et al., "Factor Xa Inhibitors," Expert Opinion on Therapeutic Patents, 9(7), 23 pages, 1999.
Hirsh, Jack et al., "Beyond Unfractionated Heparin and Warfarin: Current and Future Advances," Circulation, Journal of the American Heart Association, vol. 116, 10 pages, Jul. 31, 2007.
European Search Report, Application No. 11008623.8, 4 pages, Apr. 10, 2012.

* cited by examiner

*Primary Examiner* — Ralph Gitomer
(74) *Attorney, Agent, or Firm* — King & Spalding L.L.P.

(57) ABSTRACT

A method for determining the activity of a proteolytic coagulation factor in a sample may include (a) providing and incubating a reaction mixture comprising (i) the sample, (ii) an agent for direct or indirect activation of the proteolytic coagulation factor in the sample, (iii) a cleavable substrate which has at least one cleavage site for the activated coagulation factor, (iv) a solid phase to which the cleavable substrate is bound or becomes bound during the incubation; (b) separating off the solid phase; and (c) determining the amount of solid-phase-bound, uncleaved substrate, wherein the determined amount of solid-phase-bound, uncleaved substrate indicates a quantitative measure of the activity of the proteolytic coagulation factor in the sample.

18 Claims, 1 Drawing Sheet

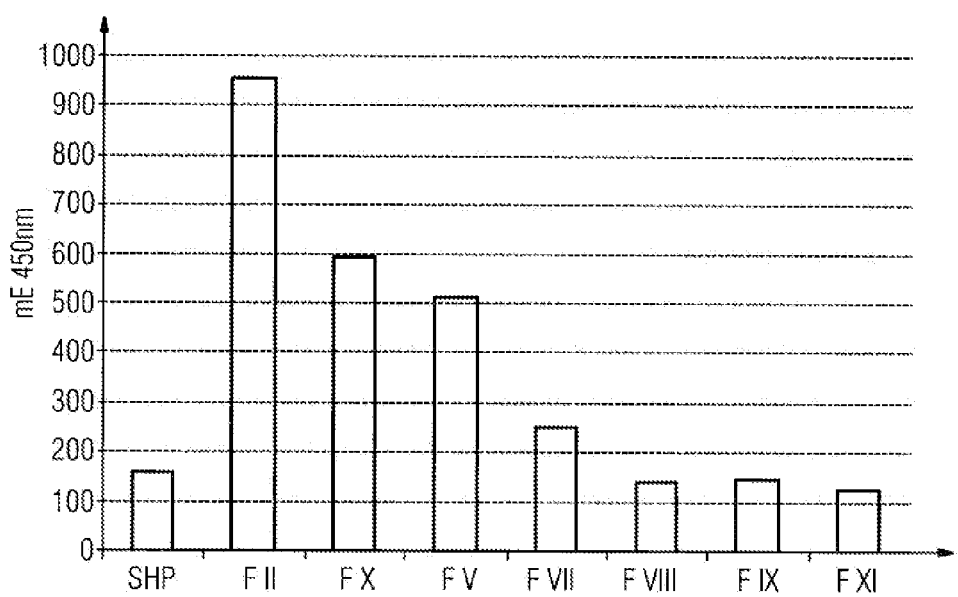
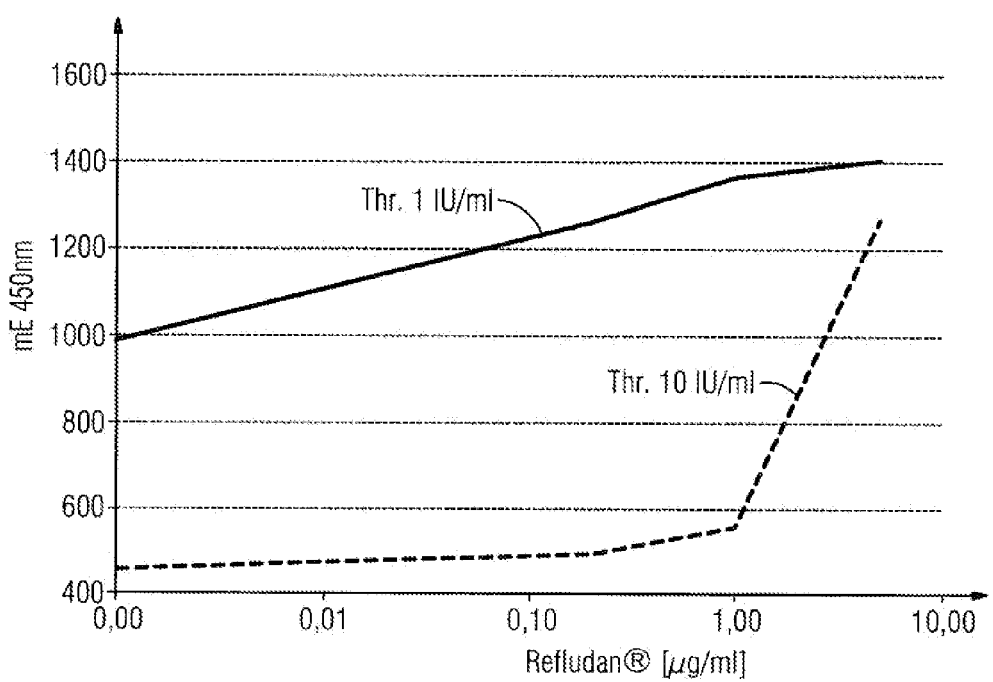

US 8,809,007 B2

METHOD FOR DETERMINING THE ACTIVITY OF A PROTEOLYTIC COAGULATION FACTOR IN A SAMPLE

CROSS-REFERENCE TO RELATED APPLICATIONS

This application is a continuation of Ser. No. 12/960,023 filed Dec. 3, 2010, now U.S. Pat. No. 8,501,429, which claims priority to EP Patent Application No. 09015240 filed Dec. 9, 2009, the contents of which are incorporated herein by reference in its entirety.

TECHNICAL FIELD

The present invention lies in the field of coagulation diagnostics and relates to methods for determining the activity of proteolytic blood coagulation factors and also to methods for determining anticoagulants, which inhibit the activity of blood coagulation factors.

BACKGROUND

Coagulation diagnostics are divided into global tests for examining the functionality of the blood coagulation cascade and individual tests for determining the activity of individual blood coagulation factors. Different test formats are known for both global tests and individual tests. Test formats are essentially divided into coagulation tests and chromogenic tests.

In a coagulation test, the patient sample to be examined, which usually consists of plasma, is mixed with a coagulation activator which starts the coagulation process. The coagulation process leads to the formation of a fibrin clot which can be measured with the aid of photometric methods. The rate of fibrin formation is a measure of the functionality of the blood coagulation cascade. To determine the activity of an individual coagulation factor in a coagulation test, the patient sample to be examined is additionally mixed with deficient plasma which supplies all components of the blood coagulation cascade except the blood coagulation factor to be tested.

In a chromogenic test, the patient sample to be examined, which usually consists of plasma, is mixed with a coagulation activator and with a substrate for a coagulation factor. Since most blood coagulation factors are serine endopeptidases, i.e., hydrolases which can cleave peptide bonds, use is predominantly made of peptide substrates which are cleaved highly specifically by the blood coagulation factor to be determined and which have a detectable signaling moiety. It may be preferred to use cleavable chromogenic or fluorogenic signalling moieties which are determined photometrically. Patent documents EP 34122 A1 and U.S. Pat. No. 4,508,644 describe a multiplicity of chromogenic peptide substrates and the use thereof in coagulation diagnostic tests, e.g., for determining the coagulation factors factor IIa (thrombin) and Xa. In document EP 78764 A1, a chromogenic method for determining the coagulation factor XIIa is described.

Particularly chromogenic tests can also be used to determine anticoagulants, which inhibit the activity of blood coagulation factors, in patient samples. For this purpose, the patient sample to be examined is mixed with an activated coagulation factor and with a substrate for this coagulation factor. The more anticoagulant that is present in the sample, the stronger is the inhibition of the activated coagulation factor and the less substrate that is cleaved.

These known methods are homogeneous methods. Homogeneous test methods have the advantage that the sample is mixed with the detection reagents to form a test mix and that the detection reaction is measured in this test mix without the need for additional separation steps, for example, for separating the analyte from the rest of the sample constituents. Homogeneous test methods, however, also have the disadvantage that substances intrinsic to the sample are present during the entire test method and, as a result, can affect the detection reaction or can interfere with the measurement of the detection reaction. Patient samples can, for example in individual cases, contain abnormally high concentrations of one or more intrinsic, i.e., endogenous substances, which can prove disruptive on exceeding a tolerable concentration in photometric detection methods and can lead to a systematic error. It is well known that problems are caused by hemolytic, icteric, and/or lipemic serum or plasma samples, so-called HIL samples which have abnormally high concentrations of hemoglobin, bilirubin, and/or triglyceride. Abnormally high concentrations of these interfering substances can be caused by a pathological state of the patient or else by inappropriate sample acquisition or storage.

SUMMARY

According to various embodiments, a method for determining the activity of proteolytic coagulation factors in a sample can be provided which is less susceptible to interference by disruptive substances intrinsic to the sample.

According to an embodiment, a method for determining the activity of a proteolytic coagulation factor in a sample may comprise the following steps:
  a. providing and incubating a reaction mixture comprising
     i. the sample,
     ii. an agent for direct or indirect activation of the proteolytic coagulation factor in the sample,
     iii. a cleavable substrate which has at least one cleavage site for the activated coagulation factor,
     iv. a solid phase to which the cleavable substrate is bound or becomes bound during the incubation;
  b. separating off the solid phase; and
  c. determining the amount of solid-phase-bound, uncleaved substrate.

According to a further embodiment, the cleavable substrate can be present in a separate reagent which is added to the reaction mixture, and wherein the reaction mixture may comprise a solid phase to which the cleavable substrate becomes bound during the incubation. According to a further embodiment, the cleavable substrate may comprise a peptide which consists of 3 to 150 amino acid residues. According to a further embodiment, the cleavable substrate can be a natural substrate for the activated coagulation factor and a constituent of the sample, and wherein the reaction mixture comprises a solid phase to which the cleavable substrate becomes bound during the incubation. According to a further embodiment, the reaction mixture may comprise a solid phase to which the cleavable substrate is covalently bonded. According to a further embodiment, the cleavable substrate may have a first binding partner A of a first binding pair A/B, and wherein the solid phase has the second binding partner B of the first binding pair A/B, and wherein the cleavable substrate is bound to the solid phase by the binding of binding partners A and B or becomes bound during the incubation. According to a further embodiment, the binding partners A and B can be chosen such that they form a binding pair A/B selected from the group consisting of FLAG-tag/anti-FLAG-tag antibody, His-tag/anti-His-tag antibody, fluorescein/anti-fluorescein antibody. According to a further embodiment, the cleavable substrate may have a first binding partner X of a second binding pair X/Y, and wherein the second binding partner Y of the second binding pair X/Y is associated with a component of a signal-producing system. According to a further embodiment, the binding partners X and Y can be chosen such that they form a binding pair X/Y selected from the group consisting of biotin/avidin, biotin/streptavidin. According to a further embodiment, an agent selected from the group consisting of thromboplastin, factor IIa, factor VIIa, factor IXa, factor Xa, factor XIa, factor XIIa, activated protein C, snake poisons, negatively charged phospholipids, calcium ions, tissue factor, silica, kaolin, ellagic acid, and celite may be used for direct or indirect activation of the proteolytic coagulation factor. According to a further embodiment, an inhibitor of fibrin aggregation may further be added to the reaction mixture.

According to another embodiment, the above described method may be used for determining the activity of a proteolytic coagulation factor selected from the group consisting of factor II, factor VII, factor IX, factor X, factor XI, factor XII, and protein C.

According to yet another embodiment, a method for quantitatively determining an anticoagulant in a sample may comprises the following steps:
 a. providing and incubating a reaction mixture comprising
  i. the sample,
  ii. a defined amount of an activated coagulation factor whose activity is directly or indirectly influenceable by the anticoagulant to be determined, wherein the activated coagulation factor is present in a separate reagent which is added to the reaction mixture,
  iii. a cleavable substrate which has at least one cleavage site for the activated coagulation factor,
  iv. a solid phase to which the cleavable substrate is bound or becomes bound during the incubation;
 b. separating the solid phase; and
 c. determining the amount of solid-phase-bound, uncleaved substrate.

According to a further embodiment, the above method may be used for quantitatively determining an anticoagulant selected from the group consisting of LMW heparin, HMW heparin, heparinoids, direct thrombin inhibitors, and direct factor Xa inhibitors. According to a further embodiment, the reaction mixture may comprise a defined amount of an activated coagulation factor selected from the group consisting of factor IIa and factor Xa.

BRIEF DESCRIPTION OF THE DRAWINGS

FIG. 1 shows the absorbance values at 450 nm of samples in which the extrinsic pathway of coagulation was activated and in which thrombin activity was determined, FIG. 2 shows the absorbance values at 450 nm of samples, having different concentrations of Refludan®

DETAILED DESCRIPTION

As stated above, a method may comprise the following steps:
 a. providing and incubating a reaction mixture comprising
  i. the sample,
  ii. an agent for direct or indirect activation of the proteolytic coagulation factor in the sample,
  iii. a cleavable substrate which has at least one cleavage site for the activated coagulation factor,
  iv. a solid phase to which the cleavable substrate is bound or becomes bound during the incubation;
 b. separating off the solid phase; and
 c. determining the amount of solid-phase-bound, uncleaved substrate.

The amount of uncleaved substrate bound to the solid phase is inversely proportional to the activity of the proteolytic coagulation factor to be determined.

Providing the reaction mixture always comprises contacting the sample, preferably a blood or plasma sample, with an agent for direct or indirect activation of the proteolytic coagulation factor to be determined in the sample and with a solid phase. The cleavable substrate, which has at least one cleavage site for the activated coagulation factor, can be added to the reaction mixture in different ways:

The cleavable substrate, for example a synthetic peptide or a purified protein which is not bound to a solid phase, can be present in a separate reagent which is added to the reaction mixture. The reaction mixture then comprises a solid phase to which the cleavable substrate becomes bound during the incubation.

The cleavable substrate, for example a synthetic peptide or a purified protein, is already bound to the solid phase and is, together with the solid phase as a constituent thereof, contacted with the sample and the agent for activation of the proteolytic coagulation factor.

The cleavable substrate is a natural substrate for the activated coagulation factor and naturally occurring in the sample and is, as a result, added to the reaction mixture with the sample as a constituent of the sample material. The reaction mixture then comprises a solid phase to which the cleavable natural substrate becomes bound during the incubation.

Cleavable substrates which have at least one cleavage site for an activated coagulation factor are well known to a person skilled in the art. A cleavable substrate can be a synthetically, recombinantly, or biotechnologically produced molecule or a natural molecule which is broken up into two cleavage products through the action of the activated coagulation factor. A cleavable substrate can consist wholly or partly of a peptide. Preferably, it may comprise a peptide portion at least in the region of the cleavage site. Preferably, the peptide portion of a cleavable substrate may consist of 3 to about 150 amino acid residues.

In another embodiment, the cleavable substrate can consist of a complete protein or of a protein fragment. A cleavable substrate can also be a natural substrate of an activated coagulation factor. An example of a natural cleavable substrate is factor V, which has cleavage sites for activated protein C, factor Xa, factor IIa (thrombin), and plasmin. A further example is fibrinogen, which has cleavage sites for factor IIa (thrombin). Yet a further example is factor II (prothrombin), which has cleavage sites for factor IIa (thrombin), factor Xa, and various snake poisons, such as, for example, ecarin or textarin.

In an embodiment of the method, the cleavable substrate, which has at least one cleavage site for the activated coagulation factor, is bound to a solid phase.

The term "bound" is to be understood broadly and comprises, for example, covalent bonding and noncovalent binding, direct and indirect binding, adsorption to a surface, and inclusion in an indentation or a cavity, etc. In the case of covalent bonding, the cleavable substrate is bound to the solid phase via a chemical bond. Examples of noncovalent binding are surface adsorption, inclusion in cavities, or the binding of two specific binding partners. In addition to direct binding to the solid phase, the cleavage substrate can also be bound indirectly to the solid phase via a specific interaction with other specific binding partners.

In an embodiment, the cleavable substrate has a first binding partner A of a first binding pair A/B, and the solid phase has the binding partner B, and the substrate is bound to the solid phase by the binding of binding partners A and B.

In another embodiment of the method, the cleavable substrate, which has at least one cleavage site for the activated coagulation factor, becomes bound to the solid phase during the incubation of the reaction mixture. For this purpose, the cleavable substrate has a first binding partner A of a first binding pair A/B, and the solid phase has the binding partner B, and the substrate becomes bound to the solid phase by the binding of binding partners A and B during the incubation of the reaction mixture.

Suitable binding pairs A/B are, in particular, antigen/antibody combinations, wherein the binding partner A is an antigenic epitope of the cleavable substrate. The antigenic epitope can be a natural linear or conformational epitope of a natural protein or protein fragment, more particularly when a natural substrate present in the sample is used as a cleavable substrate. The antigenic epitope can also be a heterologous linear or conformational epitope of a modified cleavable substrate. Examples of heterologous linear or conformational epitopes are FLAG- or His- or fluorescein tags which are used more particularly for labeling peptides or proteins. The solid-phase-bound binding partner B must be chosen such that the cleavable substrate can become specifically bound. Preferably, the binding partner B may consist of an antibody or an antigen-binding fragment thereof. Particularly preferred binding pairs A/B may be FLAG-tag/anti-FLAG-tag antibody, His-tag/anti-His-tag antibody, and fluorescein/anti-fluorescein antibody.

In a further embodiment of the method, the cleavable substrate has a first binding partner X of a second binding pair X/Y which interacts with the second binding partner Y of the second binding pair X/Y, wherein the second binding partner Y is associated with a component of a signal-producing system. In this way, uncleaved substrate can be detected. The binding partner X is arranged in a substrate region which, provided the substrate is cleaved by the activated proteolytic coagulation factor, is separated from the solid-phase-bound region of the substrate.

Suitable binding pairs X/Y are, for example, antigen/antibody combinations, wherein the binding partner X is an antigenic epitope of the cleavable substrate. The antigenic epitope can be a natural linear or conformational epitope of a natural protein or protein fragment, more particularly when a natural substrate present in the sample is used as a cleavable substrate. The antigenic epitope can also be a heterologous linear or conformational epitope of a modified cleavable substrate. Examples of heterologous linear or conformational epitopes are FLAG- or His- or fluorescein tags which are used more particularly for labeling peptides or proteins. Further suitable binding pairs X/Y are, for example, biotin/avidin and biotin/streptavidin.

The second binding partner Y is associated with a component of a signal-producing system.

A "signal-producing system" can be one or more components, wherein at least one component is a detectable label. A label is to be understood to mean any molecule which itself produces a signal or which can induce the production of a signal, such as, for example, a fluorescent substance, a radioactive substance, an enzyme, or a chemiluminescent substance. The signal can, for example, be detected or measured by means of enzyme activity, luminescence, light absorbance, light scattering, emitted electromagnetic or radioactive radiation, or chemical reaction.

A label is itself capable of generating a detectable signal so that no further components are necessary. Many organic molecules absorb ultraviolet and visible light, whereby these molecules can enter an excited energy state and release the absorbed energy in the form of light of a wavelength other than that of the excitation light. Yet other labels, such as, for example, radioactive isotopes or dyes, can generate a detectable signal directly.

Yet other labels require further components for signal generation, i.e., the signal-producing system in such a case includes all the components required for signal production, such as, for example, substrates, coenzymes, quenchers, accelerants, additional enzymes, substances which react with enzyme products, catalysts, activators, cofactors, inhibitors, ions, etc.

Suitable labels are, for example, enzymes including horseradish peroxidase, alkaline phosphatase, glucose-6-phosphate dehydrogenase, alcohol dehydrogenase, glucose oxidase, β-galactosidase, luciferase, urease, and acetylcholinesterase; dyes; fluorescent substances including fluorescein isothiocyanate, rhodamine, phycoerythrin, phycocyanin, ethidium bromide, 5-dimethylaminonaphthalene-1-sulfonyl chloride, and fluorescent chelates of rare earths; chemiluminescent substances including luminol, isoluminol, acridinium compounds, olefin, enol ethers, enamine, aryl vinyl ethers, dioxene, arylimidazole, lucigenin, luciferin, and aequorin; sensitizers including eosin, 9,10-dibromoanthracene, methylene blue, porphyrin, phthalocyanine, chlorophyll, Rose Bengal; coenzymes; enzyme substrates; radioactive isotopes including $^{125}I$, $^{131}I$, $^{14}C$, $^{3}H$, $^{32}P$, $^{33}P$, $^{35}S$, $^{51}Cr$, $^{59}Fe$, $^{57}Co$, and $^{75}Se$.

The solid phase to which the cleavable substrate is bound or becomes bound during the incubation comprises an article which consists of porous and/or nonporous, generally water-insoluble material and which can have a wide variety of different forms, such as, for example, those of vessels, small tubes, microtiter plates, beads, microparticles, rods, strips, filter or chromatography paper, etc. Generally, the surface of the solid phase is hydrophilic or can be made hydrophilic. The solid phase can consist of a wide variety of different materials, such as, for example, inorganic and/or organic materials, synthetic materials, naturally occurring materials and/or modified naturally occurring materials. Examples of solid phase materials are polymers, such as, for example, cellulose, nitrocellulose, cellulose acetate, polyvinyl chloride, polyacrylamide, crosslinked dextran molecules, agarose, polystyrene, polyethylene, polypropylene, polymethacrylate, or nylon; ceramic, glass, metals, more particularly noble metals such as gold and silver; magnetite; mixtures or combinations thereof; etc.

The solid phase can have a coating composed of one or more layers, for example, of proteins, carbohydrates, lipophilic substances, biopolymers, organic polymers, or mixtures thereof, in order, for example, to diminish or to prevent the nonspecific binding of sample constituents to the solid phase or, for example, to achieve improvements with regard to suspension stability of particulate solid phases, storage stability, shape-imparting stability, or resistance to UV light, microbes, or other destructively acting agents.

To directly or indirectly activate the proteolytic coagulation factor in the sample, the sample is usually mixed with an agent which causes direct or indirect activation of the proteolytic coagulation factor. Direct activation is to be understood to mean use of an agent which directly activates the proteolytic coagulation factor to be determined, irrespective of the presence of other coagulation factors. Indirect activation is to be understood to mean use of an agent which activates one or more blood coagulation factors of the blood coagulation cascade, which in turn activate the proteolytic coagulation factor to be examined. The type of agent depends on which coagulation factor is to be determined, on whether the activity of the coagulation factor alone is to be determined, or on whether the functionality of the blood coagulation cascade or of a subdomain of the blood coagulation cascade (extrinsic or intrinsic pathway) is to be determined with the aid of a coagulation factor. Substances and specific mixtures of various substances which make direct or indirect activation of proteolytic coagulation factors possible are well known to a person skilled in the art and comprise, for example, phospholipids, such as, for example, negatively charged phospholipids; lipoproteins, such as, for example, thromboplastin; proteins, such as, for example, tissue factor, activated serine proteases, such as, for example, factor IIa (thrombin), factor VIIa, factor IXa, factor Xa, factor XIa, factor XIIa, or activated protein C; snake poisons, such as, for example, PROTAC® enzyme, ecarin, textarin, noscarin, batroxobin, thrombocytin, or Russells's viper venom (RVV); contact activators, such as, for example, silica, kaolin, ellagic acid, or celite. Further substances which may comprise an agent are, for example, buffer substances, salts, detergents, ions, more particularly calcium ions and chelating agents.

A "sample" is to be understood to mean, for the purpose of the invention, the material which presumably contains the proteolytic coagulation factor to be detected. The term sample comprises, more particularly, human or animal body fluids, chiefly blood and plasma.

After provision of the reaction mixture, which comprises the sample, an agent for activation of the proteolytic coagulation factor, a cleavable substrate, and a solid phase to which the cleavable substrate is bound or becomes bound, the reaction mixture is incubated for a certain length of time in order to ensure sufficient activation of the coagulation factor, sufficient cleavage of the substrate by the activated coagulation factor, and, if appropriate, sufficient binding of the cleavable substrate or the cleavage product of the substrate to the solid phase. The term "sufficient" is to be understood to mean such that the method as a whole makes quantitative determination of the activity of the coagulation factor possible. The optimal duration of incubation of a certain test setup can be ascertained experimentally.

In an embodiment, an inhibitor of fibrin aggregation can further be added to the reaction mixture. A fibrin aggregation inhibitor is to be understood to mean a substance, more particularly a synthetic oligopeptide, which inhibits the joining together (polymerization) of fibrin monomers which arise through the action of thrombin and thus prevents clot formation in the reaction mixture (see, for example, EP 0 456 152 B1).

After the reaction mixture has been incubated, the solid phase, and thus the constituents bound to it, is separated from the rest of the constituents of the reaction mixture. Separation can be carried out in different ways, depending on the type of solid phase, for example, by centrifugation, filtration, magnetic separation, or by aspiration of the liquid phase of the reaction mixture. After removal of the solid phase, at least one wash step can be carried out in order to remove residual reaction mixture from the solid phase as completely as possible and/or to prepare the solid phase for the subsequent detection reaction. For this purpose, the solid phase is incubated with a wash solution, preferably with a buffer solution, and subsequently separated again from the wash solution.

Determining the amount of solid-phase-bound, uncleaved substrate can be carried out in different ways, depending on the type of detection system used, for example, by incubation of the solid phase with a reagent which comprises substances which interact specifically with the uncleaved substrate and generate a measurable signal. Preferably, determining the amount of solid-phase-bound, uncleaved substrate may be carried out by incubating the solid phase with a detection reagent which comprises the binding partner Y of the second binding pair X/Y, in which case binding partner Y binds specifically to the binding partner X of the uncleaved substrate. The binding partner Y can either be associated directly with a signal-giving component or become associated with a signal-giving component.

The amount or strength of the signal is proportional to the amount of solid-phase-bound, uncleaved substrate and thus inversely proportional to the activity of the proteolytic coagulation factor.

The method according to various embodiments for determining a proteolytic coagulation factor is particularly suitable for determining the proteolytic coagulation factors factor II, factor VII, factor IX, factor X, factor XI, factor XII, or protein C.

According to other embodiments, a method for quantitatively determining an anticoagulant in a sample can be provided which is less vulnerable to disruptive substances intrinsic to the sample.

According to these other embodiments, a method may comprise the following steps:
  a. providing and incubating a reaction mixture comprising
     i. the sample,
     ii. a defined amount of an activated coagulation factor whose activity is directly or indirectly influenceable by the anticoagulant to be determined, wherein the activated coagulation factor is present in a separate reagent which is added to the reaction mixture,
     iii. a cleavable substrate which has at least one cleavage site for the activated coagulation factor,
     iv. a solid phase to which the cleavable substrate is bound or becomes bound during the incubation;
  b. separating off the solid phase; and
  c. determining the amount of solid-phase-bound, uncleaved substrate.

In this method, a known, defined amount of an activated coagulation factor is added to the reaction mixture. Which activated coagulation factor is added depends on which anticoagulant is to be determined.

To determine a heparin, i.e., a high-molecular-weight, unfractionated heparin (HMW heparin) or a low-molecular-weight heparin (LMW heparin) or a heparinoid, the addition of factor IIa (thrombin) or of factor Xa is particularly suitable. To determine a direct thrombin inhibitor, for example, argatroban, melagatran, ximelagatran, bivalirudin, dabigatran, or hirudin, the addition of factor IIa (thrombin) is particularly suitable. To determine a direct factor Xa inhibitor, for example, rivaroxaban, the addition of factor Xa is particularly suitable.

The more anticoagulant that is present in the sample, the stronger is the inhibition of the activated coagulation factor that has been added and the less cleavable substrate that is cleaved. The amount of solid-phase-bound, uncleaved substrate is therefore proportional to the amount or activity, present in the sample, of the anticoagulant to be determined.

Apart from the fact that, in the method according to various embodiments for quantitatively determining an anticoagulant,
  use is made of a defined amount of an activated coagulation factor whose activity is directly or indirectly influenceable by the anticoagulant to be determined, wherein the activated coagulation factor is present in a separate reagent which is added to the reaction mixture, and that therefore the reaction mixture need not contain an agent for activating a proteolytic coagulation factor, the above explanations for carrying out the method for determining a proteolytic coagulation factor also apply to the method according to various embodiments for quantitatively determining an anticoagulant.

The following examples serve to illustrate the present invention and are not to be understood as limiting.

DESCRIPTION OF THE FIGURES

FIG. 1

FIG. 1 shows the absorbance values at 450 nm of samples in which the extrinsic pathway of coagulation was activated by Innovin® (a thromboplastin reagent) and in which thrombin activity was determined (see example 1). The samples are standard human plasma (SHP), which fully comprises all coagulation factors, and also plasmas deficient in factors of the extrinsic coagulation pathway (F II, F V, F VII, F X) or of the intrinsic coagulation pathway (F VIII, F IX, F XI). Depending on the amount of thrombin in the activated sample, which is in turn dependent on the presence of the factors of the extrinsic coagulation pathway, the thrombin-sensitive peptide substrate is cleaved. The more thrombin that is present in the sample, the more thrombin substrate that is cleaved and the less uncleaved thrombin substrate that can be detected. The measured absorbance values are thus inversely proportional to the thrombin activity in the sample, i.e., to the activity of the extrinsic coagulation cascade. In the experiment shown, all plasmas deficient in factors of the extrinsic coagulation pathway (more particularly the F II-deficient plasma) therefore have higher absorbance values than normal plasma (SHP), whereas plasma lacking factors not involved in the extrinsic coagulation pathway (factor VIII, IX, XI) show no differences in signal compared to SHP. Therefore, using the test shown, it was possible to clearly detect a deficiency in factors of the extrinsic coagulation pathway in plasmas.

FIG. 2

FIG. 2 shows the absorbance values at 450 nm of samples, having different concentrations of Refludan®, to which defined amounts of thrombin were added (thr. 1 IU/ml, thr. 10 IU/ml) and in which thrombin activity was determined (see example 2). The more of the direct thrombin inhibitor Refludan® that is present in a sample, the more of the added thrombin that is inhibited, the less thrombin substrate that is cleaved, and the more uncleaved thrombin substrate that can be detected. The measured absorbance values are thus proportional to the thrombin-inhibiting activity of the Refludan® in the sample. It was evident that the sensitivity of the method is particularly good for samples having therapeutically low Refludan® concentrations (to 1 μg/ml) upon addition of a comparatively low amount of thrombin (1 IU/ml), while the sensitivity of the method is particularly good for samples having therapeutically high Refludan® concentrations (1-5 μg/ml) upon addition of a comparatively high amount of thrombin (10 IU/ml).

EXAMPLES

Example 1

Method for Determining Thrombin Activity

First, microtiter plates (Nunc-Thermo Fisher, Roskilde, Denmark) were coated with a monoclonal FLAG-epitope-specific antibody (MAK M2, Sigma Aldrich, Munich, Germany). Subsequently, a thrombin-specific peptide substrate comprising seven amino acid residues, specifically leucine, valine, proline, arginine, glycine, phenylalanine, glycine in said sequence, which has a FLAG-tag epitope at the amino-terminal end, and which is biotinylated at the carboxy-terminal end was incubated with the solid-phase-bound anti-FLAG antibody and thus bound to the solid phase. To each well, the following reagents were subsequently added in the following order:

25 μl of a fibrin aggregation inhibitor solution (6 mg/ml of a synthetic oligopeptide having the amino acid residues glycine, proline, arginine, proline, alanine in said sequence); 25 μl of sample; and 25 μl of Innovin® (recombinant human tissue factor having synthetic phospholipids, Siemens Healthcare Diagnostics, Marburg, Germany) as a coagulation activator.

Standard human plasma (SHP) and plasmas deficient in coagulation factor (factor II, factor X, factor V, factor VII, factor VIII, factor IX, factor XI) were used as samples.

The reaction mixture was commixed and incubated at 37° C. for 15 minutes. The reaction mixture was then aspirated, and each well was washed three times with, in each case, 250 μl of wash buffer. To detect uncleaved, solid-phase-bound thrombin substrate, 100 μl of a streptavidin/peroxidase (POD) conjugate solution (0.33 μg/ml, Sigma Aldrich) were added to each well and in turn incubated at 20-25° C. for 30 minutes. The conjugate solution was then aspirated, and each well was washed three times with, in each case, 250 μl of wash buffer. Subsequently, 100 μl of a buffer solution comprising 0.5 g/L TMB (3,3',5,5'-tetramethylbenzidine dihydrochloride) and 0.1 g/L hydrogen peroxide were added to each well and in turn incubated at 20-25° C. for 30 minutes. To terminate the peroxidase reaction, 100 μl of 0.5 N sulfuric acid were added to each well, and the absorbance at 450 nm minus the absorbance at reference wavelength 650 nm was determined by means of Sunrise® MTP photometer (Tecan Trading AG, Switzerland).

The results are displayed in FIG. 1.

Example 2

Method for Quantitatively Determining the Direct Thrombin Inhibitor Refludan®

As described in example 1, a thrombin-specific peptide substrate, comprising seven amino acid residues, which has a FLAG-tag epitope at the amino-terminal end and is biotinylated at the carboxy-terminal end was bound to the solid phase (microtiter plate) via an anti-FLAG antibody.

To each well, the following reagents were added in the following order:

50 μl of a fibrin aggregation inhibitor solution (3 mg/ml of a synthetic oligopeptide having the amino acid residues glycine, proline, arginine, proline, alanine in said sequence);

25 μl of sample; and

25 μl of bovine α-thrombin solution (4 or 40 IU of bovine α-thrombin per ml, 10 KIE/ml aprotinin, 150 mM/L NaCl, 5 mg/ml bovine serum albumin, 10 mg/ml mannitol, 5 μg/ml hexadimethrine bromide).

Through the different thrombin concentrations, sensitivity in various therapeutic areas can be ensured.

Standard human plasma (SHP) and normal human citrate plasma samples were used as samples. These samples were aliquoted, and Refludan® (lepirudin, recombinant hirudin, CSL Behring GmbH, Marburg, Germany) was added to each aliquot to give final concentrations of 0.0 µg/ml, 0.2 µg/ml, 1.0 µg/ml, and 5 µg/ml.

The detection of uncleaved, solid-phase-bound thrombin substrate was carried out as described in example 1, and the absorbance at 450 nm minus the absorbance at reference wavelength 650 nm was determined by means of Sunrise® MTP photometer (Tecan Trading AG, Switzerland).

The results are displayed in FIG. 2.

What is claimed is:

1. A method for determining the activity of a proteolytic coagulation factor in a sample, wherein the method comprises the following steps:
   a. providing and incubating a reaction mixture comprising
      i. the sample,
      ii. an agent for direct or indirect activation of the proteolytic coagulation factor in the sample,
      iii. a cleavable substrate which has at least one cleavage site for the activated coagulation factor,
      iv. a solid phase to which the cleavable substrate is bound or becomes bound during the incubation;
   b. separating off the solid phase; and
   c. determining the amount of solid-phase-bound, uncleaved substrate, wherein the determined amount of solid-phase-bound, uncleaved substrate indicates a quantitative measure of the activity of the proteolytic coagulation factor in the sample.

2. The method as claimed in claim 1, wherein the cleavable substrate is present in a separate reagent which is added to the reaction mixture, and wherein the reaction mixture comprises a solid phase to which the cleavable substrate becomes bound during the incubation.

3. The method as claimed in claim 2, wherein the cleavable substrate comprises a peptide which consists of 3 to 150 amino acid residues.

4. The method as claimed in claim 1, wherein the cleavable substrate is a natural substrate for the activated coagulation factor and a constituent of the sample, and wherein the reaction mixture comprises a solid phase to which the cleavable substrate becomes bound during the incubation.

5. The method as claimed in claim 1, wherein the reaction mixture comprises a solid phase to which the cleavable substrate is covalently bonded.

6. The method as claimed in claim 1, wherein the cleavable substrate has a first binding partner A of a first binding pair A/B, and wherein the solid phase has the second binding partner B of the first binding pair A/B, and wherein the cleavable substrate is bound to the solid phase by the binding of binding partners A and B or becomes bound during the incubation.

7. The method as claimed in claim 6, wherein the binding partners A and B are selected to form a binding pair A/B selected from the group consisting of FLAG-tag/anti-FLAG-tag antibody, His-tag/anti-His-tag antibody, fluorescein/anti-fluorescein antibody.

8. The method as claimed in claim 1, wherein the cleavable substrate has a first binding partner X of a second binding pair X/Y, and wherein the second binding partner Y of the second binding pair X/Y is associated with a component of a signal-producing system.

9. The method as claimed in claim 8, wherein the binding partners X and Y are selected to form a binding pair X/Y selected from the group consisting of biotin/avidin, biotin/streptavidin.

10. The method as claimed in claim 1, wherein the activation agent is selected from the group consisting of thromboplastin, factor IIa, factor VIIa, factor IXa, factor Xa, factor XIa, factor XIIa, activated protein C, snake poisons, negatively charged phospholipids, calcium ions, tissue factor, silica, kaolin, ellagic acid, and celite is used for direct or indirect activation of the proteolytic coagulation factor.

11. The method as claimed in claim 1, wherein an inhibitor of fibrin aggregation is further added to the reaction mixture.

12. The method as claimed in claim 1, wherein the step of separating off the solid phase is performed by centrifugation, filtration, magnetic separation, or by aspiration of the liquid phase of the reaction mixture.

13. The method as claimed in claim 1, wherein after removal of the solid phase, at least one wash step is carried out.

14. The method as claimed in claim 13, wherein the solid phase is incubated with a wash solution and subsequently separated again from the wash solution.

15. The method as claimed in claim 14, wherein the wash solution is a buffer solution.

16. The method as claimed in claim 1, wherein the method is used for determining the activity of a proteolytic coagulation factor selected from the group consisting of factor II, factor VII, factor IX, factor X, factor XI, factor XII, and protein C.

17. The method as claimed in claim 13 for quantitatively determining an anticoagulant selected from the group consisting of LMW heparin, HMW heparin, heparinoids, direct thrombin inhibitors, and direct factor Xa inhibitors.

18. The method as claimed in claim 13, wherein the reaction mixture comprises a defined amount of an activated coagulation factor selected from the group consisting of factor IIa and factor Xa.

* * * * *